(12) United States Patent
McDonald

(10) Patent No.: US 11,820,565 B2
(45) Date of Patent: Nov. 21, 2023

(54) STERILE BARRIER PACKAGING SYSTEM

(71) Applicant: Sonoco Development, Inc., Hartsville, SC (US)

(72) Inventor: Todd LaMont McDonald, Sycamore, IL (US)

(73) Assignee: Sonoco Development, Inc., Hartsville, SC (US)

( * ) Notice: Subject to any disclaimer, the term of this patent is extended or adjusted under 35 U.S.C. 154(b) by 160 days.

(21) Appl. No.: 17/190,546

(22) Filed: Mar. 3, 2021

(65) Prior Publication Data
US 2021/0284406 A1 Sep. 16, 2021

Related U.S. Application Data

(60) Provisional application No. 62/988,017, filed on Mar. 11, 2020.

(51) Int. Cl.
*B65D 51/24* (2006.01)
*A61B 50/33* (2016.01)
*B65D 1/34* (2006.01)
*G06K 19/06* (2006.01)
*G06K 7/14* (2006.01)
*A61B 50/00* (2016.01)

(52) U.S. Cl.
CPC .......... *B65D 51/245* (2013.01); *A61B 50/33* (2016.02); *B65D 1/34* (2013.01); *G06K 7/1413* (2013.01); *G06K 7/1417* (2013.01); *G06K 19/06028* (2013.01); *G06K 19/06037* (2013.01); *A61B 2050/0065* (2016.02)

(58) Field of Classification Search
CPC ....... G06K 19/06037; G06K 19/06028; G06K 7/1417; G06K 7/1413; B65D 1/34; B65D 51/245; A61B 2050/0065; A61B 50/33
USPC .......................................................... 206/438
See application file for complete search history.

(56) References Cited

U.S. PATENT DOCUMENTS

| | | | |
|---|---|---|---|
| 7,806,322 B2 | 10/2010 | Brundage et al. | |
| 8,542,099 B2 | 9/2013 | Pizzuto | |
| 9,463,137 B2 | 10/2016 | Domanik | |
| 10,010,636 B2 | 7/2018 | Henniges et al. | |
| 10,904,474 B2 * | 1/2021 | Han ........................ | G11B 27/19 |
| 2009/0191531 A1 * | 7/2009 | Saccocci ................. | G09B 5/062 600/26 |
| 2011/0127188 A1 * | 6/2011 | Thompson .............. | B65D 77/20 206/524.6 |
| 2014/0111333 A1 * | 4/2014 | Haas ....................... | G08B 23/00 340/539.11 |
| 2015/0224247 A1 * | 8/2015 | McDorman ............. | A61L 2/087 206/569 |
| 2016/0030368 A1 * | 2/2016 | Atkins, Jr. .............. | A61B 17/24 206/572 |
| 2017/0224435 A1 * | 8/2017 | Godfrey .................. | A61B 50/33 |

(Continued)

FOREIGN PATENT DOCUMENTS

| | | | | |
|---|---|---|---|---|
| CA | 2653280 A1 * | 11/2006 | ............. | A61B 90/90 |
| CA | 2534596 A1 | 9/2007 | | |

(Continued)

*Primary Examiner* — Rafael A Ortiz
(74) *Attorney, Agent, or Firm* — von Briesen & Roper, s.c.

(57) ABSTRACT

A sterile barrier system package comprising a tray, a lidding film and a unique printed or molded SBS Code for communicating and tracking the SBS to its specific intended usability through activating a digital experience.

15 Claims, 2 Drawing Sheets

(56) References Cited

U.S. PATENT DOCUMENTS

2018/0082480 A1\* 3/2018 White .................... G06T 11/00
2019/0053962 A1\* 2/2019 Lavon ................. A61F 13/0246

FOREIGN PATENT DOCUMENTS

WO     WO2019190560    \* 10/2019
WO     WO-2019190560 A1 \* 10/2019    ............ A61B 50/33

\* cited by examiner

STERILE BARRIER PACKAGING SYSTEM

BACKGROUND

Field of the Invention

This patent relates to a sterile barrier system (SBS) package. More particularly, this patent relates to an SBS package comprising a sterile package and a machine readable code for communicating data and information and for tracking the SBS package to its specific intended usability through activating a digital experience.

Description of the Related Art

The use of sterile items in medical procedures is critical to the prevention of spreading harmful and infectious microbes to patients. For this reason items used in medical procedures often are packaged in sterile thermoformed trays having peel off enclosures.

Currently there is no easy and effective way to communicate how an item should be sterilely presented from the thermoformed tray to the sterile field in the operating room. The present disclosure addresses this need.

SUMMARY OF THE INVENTION

The present disclosure relates to a sterile barrier system package comprising a sterile package and a code for communicating data and information and for tracking the sterile barrier system (SBS) package to its specific intended usability location through activating a digital experience.

In one aspect the sterile barrier system package comprises a tray, a lidding film and a unique printed or molded "SBS Code" for the purpose of communicating and tracking the SBS package to its specific intended usability location through activating a digital experience.

In another aspect a sterile barrier system package comprises a package for holding an article and a machine readable code located on an exterior surface of the package, the machine readable code communicating data and other information relating to the package. The data and other information may be selected from the group consisting of the sterile barrier system package's sterilization, validation, stability and intended sterile presentation. The machine readable code may be used to enter data points into a blockchain.

THE DRAWINGS

DETAILED DESCRIPTION OF THE INVENTION

Figure 1:
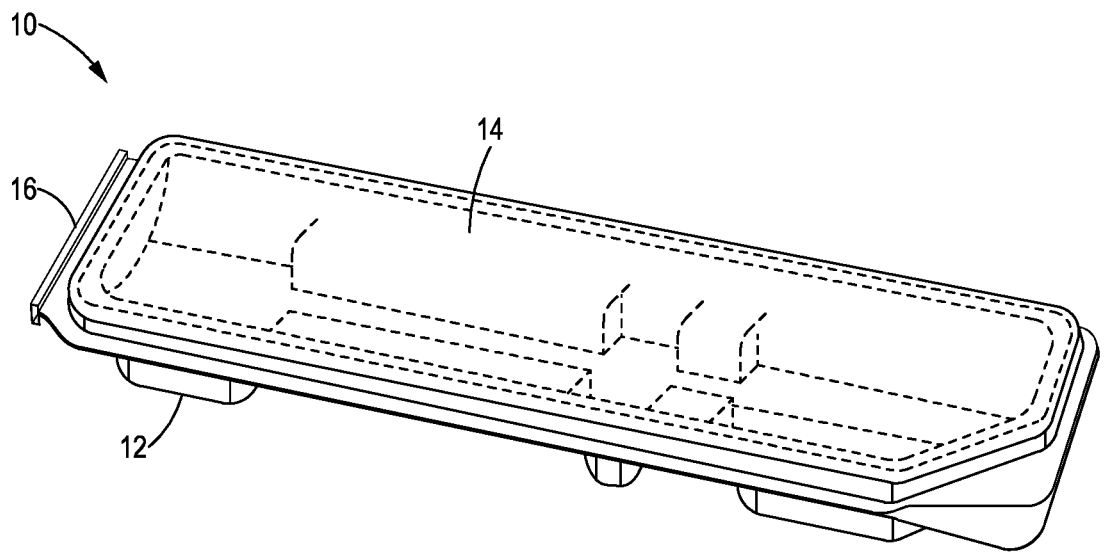
FIG. 1 is a perspective view of a conventional medical device package.

While this disclosure may be embodied in many forms, there is shown in the drawings and will herein be described in detail one or more embodiments with the understanding that this disclosure is to be considered an exemplification of the principles of the disclosure and is not intended to limit the disclosure to the illustrated embodiments.

This description relates to a sterile barrier system (SBS) package comprising a thermoformed tray and lid stock such as lidding film sealed to the top of the tray. A sterile barrier system (SBS) is a package, such as a medical package, that holds a product and keeps it sterile during its travel through the supply chain until it gets to the user, typically someone in an operating room.

The sterile barrier system (SBS) package comprises a machine readable code used to communicate data and information and to track the SBS package to its specific intended usability, such as by activating a specific digital experience.

Background: Thermoformed Packaging of Medical Devices

FIG. 1 is a perspective view of a conventional medical device package 10. The package 10 may be a plastic thermoformed package manufactured to meet or exceed standards set for medical device packaging. The package 10 illustrated in FIG. 1 comprises a tray 12 and a lid 14. The package 10 defines a cavity for holding a medical device (not shown) such as a syringe. The package 10 may be sealed so that the cavity is sterile.

The tray 12 may be custom designed thermoformed plastic tray to securely hold a particular item such as a syringe or other medical device. The tray 12 may be the last thing the medical device contacts before being presented to the end user.

The lid 14 may be made of clear, rigid plastic and may be attached to the tray 12 along a hinge 16. Alternatively, or in addition to a rigid lid, the tray 12 may be sealed with a flexible, peel away film (not shown in FIG. 1).

Packaging a medical device with a thermoformed package can have the following advantages:

1. Product Orientation: A nurse may need to quickly confirm a product's orientation and how to grab it. With a thermoformed tray, a nurse can be sure that the medical device stays securely in place in the intended location so he/she can remove it swiftly and confidently.
2. Handling Assurance: To make ensure a device doesn't compromise sterility, a nurse needs to control the movement of a device as its package is opened. A thermoformed package is more likely to ensure there is no unnecessary rotation or accidental removal.
3. Clarity: A nurse can find it beneficial to see and identify the product clearly so he/she can better present the device or see any potential defects.
4. Consistent Opening Experience: Incorporating a good peel area in the package design can allow a nurse an easy access point for peeling the lidding back from the package.
5. Additional protection: With rigid plastic, a medical device is protected in sensitive device areas. For example, a package can be designed so a syringe will not get depressed or otherwise damaged.

The International Organization for Standardization

The International Organization for Standardization (ISO), based in Geneva Switzerland, promulgates standards for SBS packaging. ISO is an independent, non-governmental international organization with a membership of 164 national standards bodies. Through its members, it brings together experts to share knowledge and develop voluntary, consensus-based, market relevant International Standards that support innovation and provide solutions to global challenges.

ISO Standards

International Standards provide world-class specifications for products, services and systems to ensure quality, safety and efficiency. The standards are instrumental in facilitating international trade. ISO has published 23019 International Standards and related documents, covering almost every industry, from technology to food safety to agriculture and healthcare.

ISO Standard 11607 for Medical Devices

Basically, ISO Standard 11607—"Packaging For Terminally Sterilized Medical Devices" provides the requirements and test methods for packaging intended to maintain the sterility of terminally sterilized medical devices until the point of use The document specifies requirements and test methods for materials, preformed sterile barrier systems, sterile barrier systems and packaging systems that are intended to maintain sterility of terminally sterilized medical devices until the point of use. It is applicable to industry, to health care facilities, and to wherever medical devices are placed in sterile barrier systems and sterilized. ISO Standard 11607 does not cover all requirements for sterile barrier systems and packaging systems for medical devices that are manufactured aseptically. Additional requirements can be necessary for drug/device combinations.

ISO Standard 11607 does not describe a quality assurance system for control of all stages of manufacture. Also, ISO Standard 11607 does not apply to packaging materials and/or systems used to contain a contaminated medical device during transportation of the item to the site of reprocessing or disposal.

Basically, and for the purpose of this disclosure, ISO Standard 11607 informs medical device companies of the requirements to keep and maintain a sterile barrier system from the point of packaging the device up until the package is opened and the device is used. ISO Standard 11607 also provides the requirements for the development and validation of processes including forming, sealing, and assembly of packaging used for sterilized medical devices.

Three Criteria

Under ISO Standard 11607, medical device manufacturers must be able to satisfy three criteria:

First, medical device manufacturers must be able to say "I've tested this device through the normal distribution channel and it has maintained a satisfactory level of sterilization."

Second, medical device manufacturers also have to say "I know what my sterilization process is, and that process will maintain a satisfactory level of sterilization through the normal distribution channel and during a predetermined shelf life (such as two years)." This typically is accomplished by accelerated age testing. In the case of a thermoformed tray type package, the testing must be done using the actual thermoformed tray, lid stock and adhesive that adheres the lid stock to the tray.

Third, medical device manufacturers must be able to say "When we made the SBS package, we made it in such a way that is was between the upper and lower control limits of my packaging process."

Adding to the ISO Standard

The International Organization for Standardization is adding to the ISO standard the requirement that nurses, for example, must be able to present proof to a doctor that the SBS package has in fact satisfied the three criteria of ISO Standard 11607. In other words, how can one present a device to a doctor in such a way that the doctor is assured the device has remained sterile and is not contaminated?

The New SBS Package

The present disclosure addresses this new requirement by providing an SBS package 30 comprising a sterile package 10 and a unique machine readable Sterile Barrier System (SBS) code 20.

Figure 2:
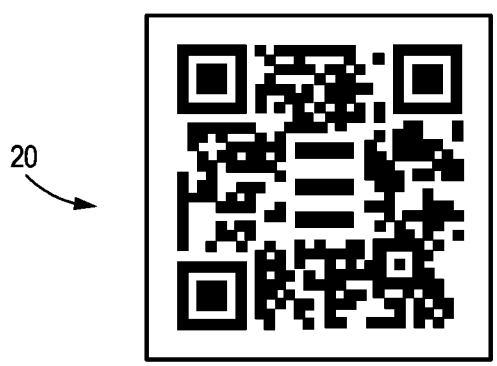
FIG. 2 shows a two dimensional, machine readable code in accordance with the disclosure.
Figure 3:
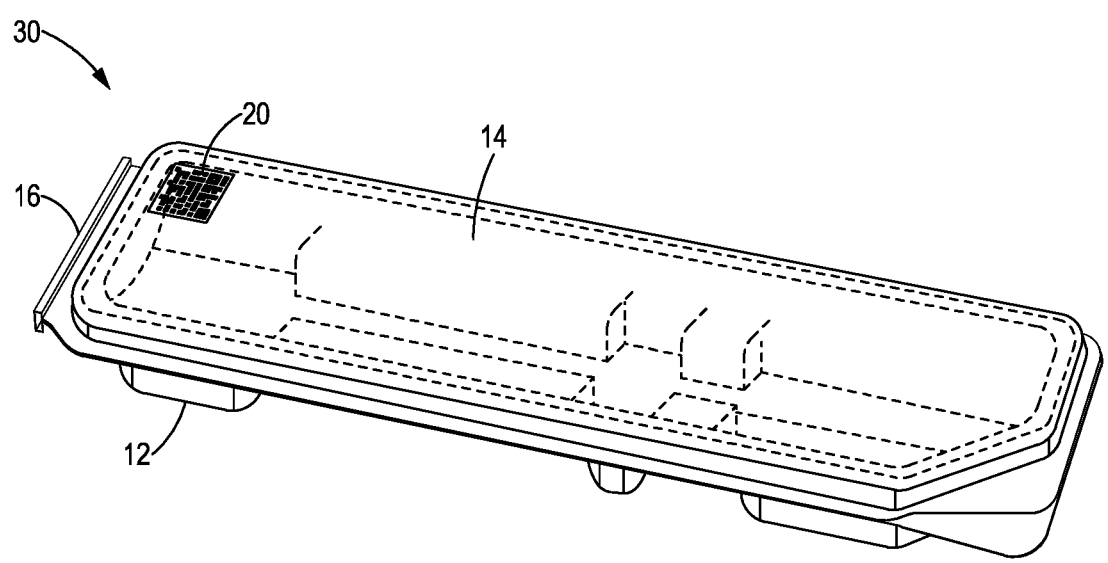
FIG. 3 is a perspective view of a sterile barrier system (SBS) package in accordance with the disclosure.

FIG. 2 shows a two dimensional, machine readable, SBS code 20 for use with an SBS package 30 in accordance with the disclosure. FIG. 3 is a perspective view of an SBS package 30 bearing an SBS code 20 in accordance with the disclosure.

The SBS package 30 comprises a package 10 and an SBS code 20 located on an external surface of the package 10. The package 10 defines a cavity for holding a medical device or other article, and may be sealed so that the cavity is sterile.

The SBS package 30 can assure a user or purchaser that the required sterile testing has been done. The SBS package 30 also can teach a user or purchaser how to use the package, for example, in the operating room.

The SBS code 20 provides a method of delivering SBS related information to the people who need it in a convenient and reliable way. For example, the SBS code 20 may be used to communicate and track the SBS package 30 to its specific intended usability location through activating a specific digital experience. Preferably the tray 12 and the SBS code 20 are difficult or impossible to counterfeit.

The SBS code 20 may be a common barcode, a two dimensional matrix code (such as a Quick Response (QR) code), a 3D code, a picture or any suitable machine readable code.

The SBS code 20 may be added to the package 10 in any suitable manner. For example, the SBS code 20 may be printed directly onto the package 10 or onto a label that is then adhered to the package 10. Alternatively, the code may be molded or embossed into the package 10. The SBS code 20 may be applied using laser marking, ultra-violet (UV) inkjet printing, laser engraving, molding or by any suitable method. Preferably the SBS code 20 is positioned on the package 10 in a location that is easily read by a machine or by the human user.

The SBS code 20 is a unique identifier, assigned to each finished/manufactured product which is ready, to be marketed or for sale.

Upon reading (scanning) the SBS code 20 with a machine (typically a mobile device such as a mobile phone or tablet computer), the machine may display a short video or a webpage where the user can view the video. The video may provide a description of how the various ISO criteria were satisfied for that particular packaged device. The SBS code 20 may provide usability data and other information on the sterile barrier system package's sterilization, validation, stability and intended sterile presentation.

The SBS code 20 may be used to confirm or validate that:
(i) The proper distribution testing has been completed for the package 10;
(ii) Stability testing has been completed for the materials that make up the package; and
(iii) Biocompatibility testing has been done and passed.

The SBS code 20 may inform the user of the parameters under which IQ/OQ/PQ were conducted. The SBS code may provide the user with a certificate of compliance that the material specifications have been met.

In addition, the SBS code 20 may communicate the validated/intended seal parameters to the sealing equipment.

The SBS code 20 may confirm/identify the sterilization method and intended dose of sterilization.

The SBS code 20 may confirm or communicate to the user the intended sterile presentation of the packaged article, and may even be used to initiate a video of the intended package opening procedure and product presentation for the nurse/user.

The SBS code 20 may confirm if the intended use of the package may or may not be susceptible to biocontamination and how the package 10 can be recycled.

The SBS code 20 may be used to prevent or deter counterfeiting.

The SBS code 20 may also be used to enter data points into a blockchain, wherein the data points are stored globally and can be accessed in near real-time by others using the same blockchain network.

Applications

The SBS package 30 can used in practice in the field (such as in an operating room). The SBS package 30 may also be used in training of medical personnel such as nurses. The SBS package 30 may also be used in the marketing and selling of medical devices to medical personnel such as doctors, nurses and hospital administrators.

It is understood that the embodiments of the disclosure described above are only particular examples which serve to illustrate the principles of the disclosure. Modifications and alternative embodiments of the disclosure are contemplated which do not depart from the scope of the disclosure as defined by the foregoing teachings and appended claims. It is intended that the claims cover all such modifications and alternative embodiments that fall within their scope.

The invention claimed is:

1. A sterile barrier system package comprising:
a sterile package comprising a thermoformed tray sealed with a flexible film, the tray and film defining a cavity;
a medical device located in the cavity; and
a machine readable code on an exterior surface of the sterile package for tracking the sterile package to an intended destination and communicating usability information about the sterile package by activating a digital experience, wherein:
the usability information includes information on whether the sterile barrier system package complies with ISO criteria for the sterile packaging of medical devices.

2. The sterile barrier system package of claim 1, further comprising:
a machine for reading the machine readable code.

3. The sterile barrier system package of claim 2 wherein: the machine is a scanning device.

4. The sterile barrier system package of claim 1 wherein: the digital experience is a video.

5. The sterile barrier system package of claim 4 wherein: the video provides a description of how the various ISO criteria were satisfied for that particular packaged device.

6. The sterile barrier system package of claim 5 wherein: the ISO criteria is ISO Standard 11607 for the packaging of medical devices.

7. The sterile barrier system package of claim 4 wherein: the video provides information on age testing of the sterile package.

8. The sterile barrier system package of claim 4 wherein: the video provides information on how to use the sterile package in an operating room.

9. The sterile barrier system package of claim 1, wherein: the machine readable code is used to initiate a video of the intended package opening procedure and product presentation.

10. A sterile barrier system package comprising:
a package for holding an article; and
a machine readable code located on an exterior surface of the package, the machine readable code communicating data and other information relating to the package; wherein:
the data and other information is selected from the group consisting of the sterile barrier system package's sterilization, validation, stability and intended sterile presentation, and
the machine readable code is used to initiate a video providing information on age testing of the package.

11. The sterile barrier system package of claim 10, wherein:
the machine readable code is used to enter data points into a blockchain.

12. The sterile barrier system package of claim 10, wherein:
the machine readable code is applied using laser marking.

13. The sterile barrier system package of claim 10, wherein:
the machine readable code is applied using ultra-violet (UV) inkjet printing.

14. The sterile barrier system package of claim 10, wherein:
the machine readable code is applied using laser engraving.

15. The sterile barrier system package of claim 10, wherein:
the machine readable code is used to initiate a video of the intended package opening procedure.

\* \* \* \* \*